United States Patent
Speck et al.

(10) Patent No.: US 6,899,708 B2
(45) Date of Patent: May 31, 2005

(54) STERILE TISSUE ACCESS SYSTEM

(76) Inventors: Ulrich Speck, Fürstendamm 20, 13465 Berlin (DE); Norbert Hosten, Hektorstrasse 17, 10711 Berlin (DE); Goran Lukic, Frohaldenstrasse 27, 8180 Bülach (CH)

( * ) Notice: Subject to any disclaimer, the term of this patent is extended or adjusted under 35 U.S.C. 154(b) by 0 days.

(21) Appl. No.: 10/250,699

(22) PCT Filed: Jan. 4, 2002

(86) PCT No.: PCT/DE02/00038
§ 371 (c)(1),
(2), (4) Date: Jul. 7, 2003

(87) PCT Pub. No.: WO02/053230
PCT Pub. Date: Jul. 11, 2002

(65) Prior Publication Data
US 2004/0049175 A1 Mar. 11, 2004

(30) Foreign Application Priority Data
Jan. 8, 2001 (DE) .......................................... 101 01 143

(51) Int. Cl.⁷ ............................................... A61B 18/24
(52) U.S. Cl. .............................. 606/15; 606/13; 606/14
(58) Field of Search ................................ 606/13–16, 41

(56) References Cited
U.S. PATENT DOCUMENTS

| | | | | |
|---|---|---|---|---|
| 5,222,953 A | | 6/1993 | Dowlatshahi | 606/15 |
| 5,895,370 A | * | 4/1999 | Edwards et al. | 604/22 |
| 5,948,008 A | * | 9/1999 | Daikuzono | 607/89 |
| 6,143,018 A | * | 11/2000 | Beuthan et al. | 607/88 |
| 6,206,847 B1 | * | 3/2001 | Edwards et al. | 604/22 |
| 6,283,957 B1 | * | 9/2001 | Hashimoto et al. | 606/15 |
| 6,283,958 B1 | * | 9/2001 | Vogl et al. | 606/15 |
| 6,428,538 B1 | * | 8/2002 | Blewett et al. | 606/46 |
| 6,464,661 B2 | * | 10/2002 | Edwards et al. | 604/22 |
| 6,506,189 B1 | * | 1/2003 | Rittman et al. | 606/41 |

FOREIGN PATENT DOCUMENTS

| | | |
|---|---|---|
| DE | 43 22 955 | 1/1994 |
| DE | 195 00 353 | 7/1996 |
| DE | 197 02 898 | 7/1998 |
| WO | WO 94/26184 | 11/1994 |

* cited by examiner

Primary Examiner—Roy D Gibson
Assistant Examiner—Henry M Johnson, III
(74) Attorney, Agent, or Firm—Miles & Stockbridge P.C.

(57) ABSTRACT

A tissue access system for tissue ablation without open surgery includes a distally open elongated tube (4) with a handle piece (6) having a through channel (7) in axial alignment with the elongated tube and an infusion fitting (9) that opens into the through channel for supplying a liquid or gaseous medium. An energy guide (16) or a catheter (10) housing such energy guide is arranged in the elongated tube and sealed from the outside. An energy-releasing zone of the energy guide is located in an energy-transparent section of the elongated tube. The medium, introduced into an annular flow channel between the energy guide or catheter and the elongated tube, serves as coolant for the energy-releasing zone and as heat transport medium in the tissue, and can also function as an ablation agent and as a contrast agent for inspection using imaging techniques.

14 Claims, 3 Drawing Sheets

STERILE TISSUE ACCESS SYSTEM

This invention relates to a sterile tissue access system that includes an energy guide at the end of which an energy-releasing zone is provided for tissue ablation without open surgery and that is shielded by, and arranged in, a non-ferromagnetic, heat-resistant, and at least distally energy-transparent elongated tube.

When using diagnostic imaging techniques such as magnetic resonance tomography, computer tomography, ultrasound and the like, it is not only possible to show the position, size, and shape of pathologic changes in the body but to carry out operations using needles, probes, and catheters without open surgery. An increasingly successful operation of this type is tissue ablation that is primarily used to eliminate tissue from spots that are difficult to access, i.e. to kill specific tissue areas that are subsequently slowly resorbed by the surrounding tissue.

As an alternative to mechanical ablation where the quantity of ablated tissue is limited by the small diameter of the medical instruments, liquids that cause tissue ablation can be administered, however with the disadvantage that such harmful liquids might flow into healthy tissue and damage it.

And finally these known devices can be used for small-diameter tissue access to kill tissue by generating thermal energy or by freezing. While cryoablation requires powerful probes and respectively large-diameter needles and catheters and is therefore limited in use, the disadvantage of thermal ablation is that it interferes with magnetic resonance tomography, an imaging technique that is used very successfully for controlling the ablation process.

It has proven beneficial for tracking and controlling thermal ablation using magnetic resonance tomography and for killing the targeted tissue area completely without damaging healthy tissue to use laser light as an energy source.

The respective tissue access systems, however, have caused the following problems when this method was used: Easy access to the tissue without unnecessary damage or injury to the patient, mechanical and thermal sensitivity of the diffusing body (energy-releasing zone) at the distal end of the laser light guide, risk of fourth-degree burning of the tissue in the vicinity of the diffusing body, exact positioning of the ablator in the tumor tissue, observation and accurate control of the ablation process regarding the completeness of the ablation, and gentle treatment of the healthy tissue. Access to the tissue is particularly problematic with sensitive tissue such as the central nervous system or the lung. As the diffusing body is fragile, steps must be taken to protect it and to prevent unnecessary mechanical strain. Fourth-degree tissue burn can be prevented by effective heat dissipation from the vicinity of the diffusing body. And finally any interference of diagnostic imaging techniques has to be prevented by appropriate methods and materials.

A respective laser application device is described, for example, in DE 196 14 780 A1. It comprises a puncture needle to be introduced into the body through the hollow shaft of which a guide wire is inserted after removing a mandrin. After the puncture needle has been taken off, a guide tube with a hollow inner mandrin in its hollow shaft is inserted via the guide wire. Subsequently, the guide wire and the hollow mandrin are removed. The guide tube that is open at its distal end comprises a T-piece at its proximal end via which local anaesthetics, lubricants, or tissue adhesives can be supplied. Moreover, this laser application system includes a distally connected sheath catheter that houses a laser light guide after its inner mandrin is removed.

The device consists of a plurality of parts and has a complex design so that a multitude of steps is required to access the tissue. The patient to be treated is also put under severe strain because the diameter of the guide tube to be introduced into the respective tissue area is rather large. While the hollow catheter protects the diffusing body, i.e. the energy-releasing zone of the light guide, from mechanical strain and damage, the laser can only be operated at a low output (up to approx. 6 watts). If the output is higher, the heat available at the tip of the sheathing catheter becomes too concentrated, which results in fourth-degree burns and destruction of the system.

While a cooling system provided according to DE 197 02 898 A1 using another sheathing catheter to prevent this disadvantage enables a relatively high laser output of up to 30 watts, the coolant that flows directly past the diffusing body of the laser light guide and is discharged outside dissipates a considerable portion of the thermal output from the tissue that will not be available for treatment. In addition, such systems are not suited for specific applications such as the central nervous system and the lungs or constitute risks and disadvantages for the patient due to the large coolant quantity required (60 ml/min) and the accordingly large cross sections of the probes and catheters and the large-diameter puncture openings.

It is therefore the problem of this invention to provide an apparatus for tissue ablation that can be controlled using imaging techniques, is of simple design and easy to handle while being highly effective with minimal effect on the patient as well as versatile.

This problem is solved according to the invention by a tissue ablation through energy supply apparatus having characteristics wherein the energy form may vary and include physical and chemical processes in the tissue.

The preferred embodiments presented as examples herein disclose important characteristics and advantageous improvements of the invention.

It is a concept of this invention that a handle piece is mounted to a distally open, elongated tube that has the shape of a needle or catheter and houses the respective energy guide, and that said handle piece is equipped with an infusion fitting connected to a through channel that is axially aligned with the elongated tube. A seal arranged in the through channel ensures airtight sealing of the respective tissue. A liquid or gaseous medium for cooling is infused directly or indirectly via the injection fitting into the energy-releasing zone of the energy guide and from there into the tissue. In this way, all the heat emitted from the energy guide is available for the ablation process while the energy-releasing zone is cooled at the same time so that the risk of damaging the tissue by fourth-degree burns due to excessive heat emission is excluded.

The liquid or gaseous medium infused into the tissue may also have a toxic or therapeutic effect that enhances the ablation process, alleviate pain and/or function as a contrasting agent for exact control and monitoring of the process using imaging techniques.

The tissue killing performed with the device according to the invention is therefore complete but still gentle, in particular with regard to adjacent healthy tissue. Another important advantage is that the elongated tube in the embodiments of the invention can be sealed towards the outside when introducing it into the tissue area to be treated that ingression of air that could have a detrimental effect on the patient is excluded. In addition, only small-diameter puncture openings are required. The energy-releasing zone of the energy guide is protected and cannot be destroyed. In addition, the apparatus that consists of a small number of parts only is also easy to handle. Tissue access can be achieved with just one puncture, which makes the unit suitable for biopsies without repeated puncturing or replacement of parts that are in contact with the body. The device according to the invention can therefore be used effectively but without risks and disadvantages for the people to be treated.

Preferable agents for infusion with the apparatus according to the invention to enhance tissue ablation are ethanol, acetic acid or acetic acid diluted in water, dimethyl sulfoxide which also improves light transmission, or dimethyl formamide.

Anaesthetics for local pain relief or cytostatics, radiopharmaceuticals and other tumor therapeuticals that prevent local and regional tumor recurrences can be infiltrated directly into the affected tissue for treatment purposes.

Preferably infused contrasting agents are iodinated compounds, paramagnetic or superparamagnetic compounds, or agents with small gas bubbles as used for X-ray methods or in magnetic resonance tomography and ultrasound diagnostics.

Gases used to enhance the ablation process are carbon monoxide and toxic gases that have a similar effect. In addition, medical gases such as carbon dioxide, oxygen, xenon, or anaesthetic gases can be supplied via the needle or the distally open catheter.

The dosage of necrosis-enhancing agents is 0.1 to 5 ml/min during and 0.5 to 50 ml/min before and after thermal tissue ablation.

In a first embodiment, the elongated tube designed according to the invention is a plastic needle in which the energy guide is arranged, and its energy-releasing zone is immediately surrounded by the supplied medium. Also, a distally closed or open and flushable catheter that houses the energy guide can be introduced into this needle with a media connection. Its outer diameter must be considerably smaller than that of the needle to provide the cross section required for the flow of the medium supplied to the needle. If the catheter is closed, the energy-releasing zone that has to stay in the needle is only cooled indirectly.

According to the invention, the energy-releasing zone of the energy guide is arranged in an area of the elongated tube that does not impede the energy and heat effect on the tissue, i.e. there is no impermeable material in the needle or catheter that would resist the heat effect or energy release. Energy transmission may also be achieved by perforating the needle or catheter wall. Needles and catheters, at least in the area of the energy-releasing zone, are preferably heat-resistant for the temperature range to be expected and transparent to energy to the extent that at least 50% of the energy generated can transfer to the tissue. When using a needle that is less energy-transparent or not energy-transparent at all, the needle end that protects the energy-releasing zone is positioned in such a way that the needle does not obstruct the energy release into the tissue.

In another embodiment, the elongated tube according to the invention is a catheter that directly houses the energy guide and that is inserted into a needle of simple design with a seal arranged at its proximal end. In this case, the supplied medium is directly applied to the energy-releasing zone of the energy guide within the catheter.

Materials used as needle or catheter material are energy and light transparent plastics such as PTFE (teflon), PEEK (polyether etherketone) or polyamide that show sufficient strength even at small wall thicknesses of 0.02 to 0.5 mm and in a diameter range of 2 mm. Alternative materials for the needles are non-ferromagnetic metals such as titanium, in which case the distal end of the catheter has to be positioned accordingly in the tissue to ensure energy release.

In an aspect of the invention, an adjustable stop is provided at the outside perimeter of the needle to limit the depth of the puncture when the needle is inserted or when the patient moves during the treatment.

According to another characteristic of the invention, a viscous sealing agent is contained in the respective needle to prevent the ingression of air.

Embodiments of the invention are explained in greater detail below with reference to the drawing that shows an enlarged view of the apparatus for tissue ablation. Wherein:

FIG. 1. shows a mandrin with a proximally mounted handle;

Figure 1:
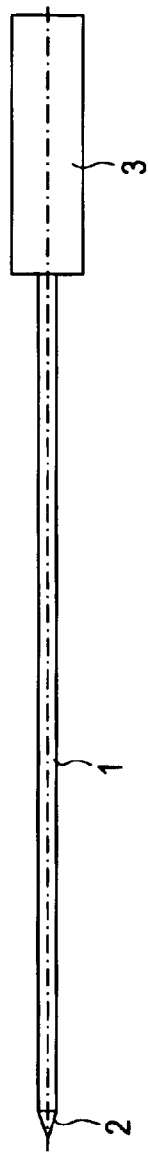
Figure 4:
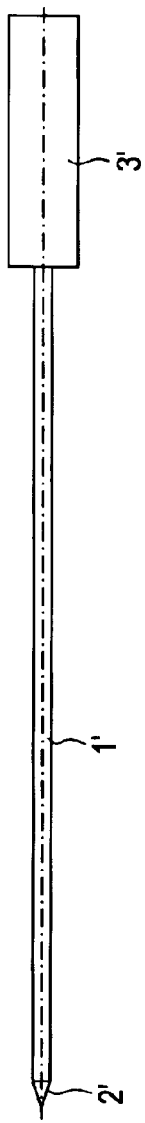
FIG. 4 shows another mandrin with a proximally mounted handle for another needle shown in FIG. 5.

The mandrin 1, 1' according to FIGS. 1 and 4 is hard to bend and comprises a tip 2, 2' and a short handle 3, 3' at its proximal end. The mandrin 1 is slightly longer than the respective needle 4, 4' according to FIGS. 2 and 5 so that its tip 2, 2' protrudes from the distal end of the needle into which the mandrin can be fitted in a gastight manner. If the energy-releasing system stays in the needle, the distal end of the needles 4,4' or the complete needles consist of energy-transparent, heat-resistant material. An adjustable stop 5 is attached to the outer perimeter of the needle 4,4' to limit puncture depth.

Figure 2:
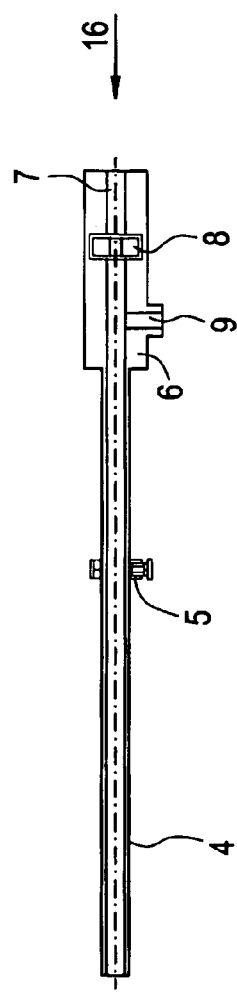
FIG. 2 shows a needle open at both sides that houses the mandrin and is filled by it, with a proximally mounted handle piece featuring an infusion fitting and a sealable axial through channel.

In a first embodiment according to FIGS. 1 and 2, the needle 4 of a design that is energy-transparent at least at its distal end is introduced into the tissue to be killed using the mandrin 1 that is located in the tube-like hollow space of the needle. An airtight seal independent of the actual seal 8 can be achieved by filling the hollow space of the needle 4 with a sterile pharmaceutical oil so that, for example, air is prevented from entering into the thorax during tissue ablation carried out in the lung. To exclude any ingression of air into the pleural cavity, the mandrin 1 is only removed from the needle 4 when the distal end of the needle 4 is positioned in the respective tissue. After taking out the mandrin 1, a commercially available light guide (energy guide) 16 with a diffusing body (energy-releasing zone) at its distal end (not shown) is inserted into the needle 4 via the axial through channel 7 of a handle piece 6 mounted to the needle 4 so that the sensitive diffusing body is located a few millimeters before the proximal opening of the needle and thus is protected from destruction. The laser light guide 16 is fixed in operating position in the through channel 7 of the handle piece 6 using a packing ring 8 (or a conduit gland, not shown) and sealed with regard to the exterior.

A cooling liquid is applied to the diffusing body at an infusion speed of 0.1 to 2 ml/min via an infusion fitting 9 that is attached to the side of the handle piece 6 and opens into the through channel 7. This prevents fourth-degree burns of the tissue in the vicinity of the diffusing body due to excessive heat. In addition, the cooling liquid that also serves as a heat transport medium is conducted to the tissue so that the heat the diffusing body generates becomes effective in the tissue and is not lost. The cooling liquid can also be designed as an ablation agent and/or contrast medium. Gas can be introduced into the needle instead of a liquid, however this eliminates the cooling effect.

As shown in FIGS. 3 and 6 through 8, tissue ablation can also be carried out using a laser light guide located in an additional catheter 10, 10' inserted into the needles 4, 4'.

Figure 3:
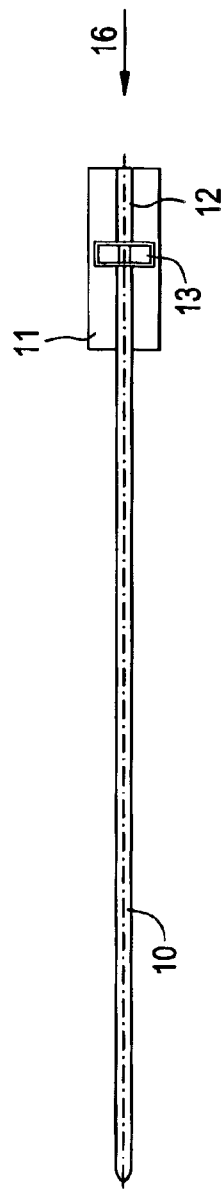
FIG. 3 shows a distally connected catheter with a handle and with a seal located in its axial through channel.
Figure 7:
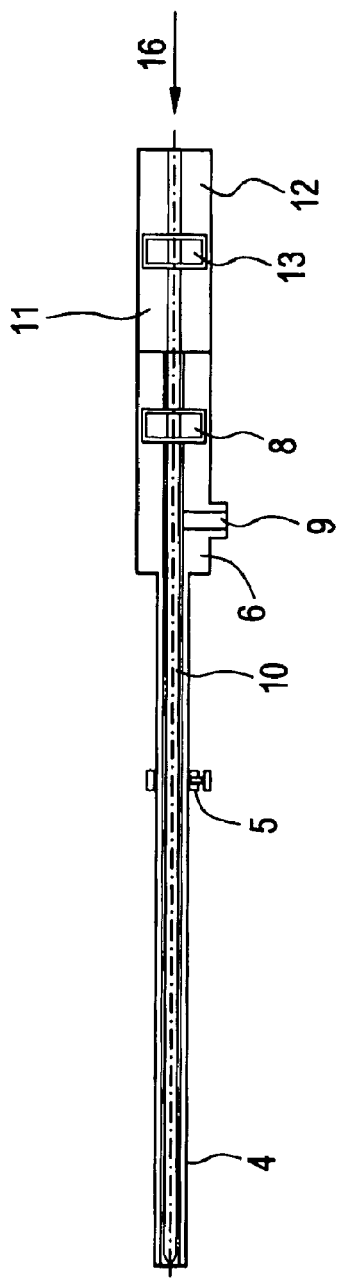
FIG. 7 shows the needle according to FIG. 2 with a distally connected catheter according to FIG. 3 inserted into it into which an energy guide can be introduced.

As FIG. 3 shows, the catheter 10 may be distally closed and proximally equipped with a handle piece 11 that comprises an axial through channel 12 and a seal 13. This catheter 10 is slid into the needle 4 after removing the mandrin 1 when the needle 4 has been properly placed in the respective tissue. The outer diameter of the catheter 10 is smaller than the inner diameter of the needle 4. Thus a hollow space with an annular cross section is created between the needle 4 and the catheter 10. The diffusing body of a laser light guide 16 to be inserted into the catheter 10 according to FIG. 7 is protected within the catheter 10 and is fixed and sealed from the outside by a seal 13 located in the handle piece 11. The catheter 10 that protrudes into the needle 4 is sealed from the outside by the packing ring 8 in the handle piece 6 and does not stretch beyond the distal opening of the needle 4 when inserted. Its distal end, like that of the needle 4, consists of an energy-transparent, heat-resistant material. Once again as described above, cooling liquid and, optionally, ablation and/or contrast liquid are indirectly conducted to the diffusing body and directly to the respective tissue section via the infusion fitting 9 in the handle piece 6 and the annular hollow space between the catheter and the needle.

Figure 5:
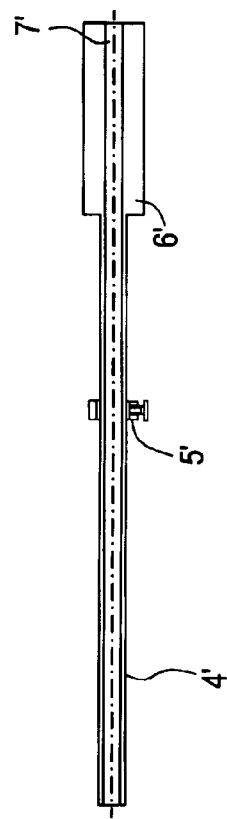
FIG. 5 shows a needle with a proximally mounted handle in which a through channel is arranged flush with the needle.
Figure 6:
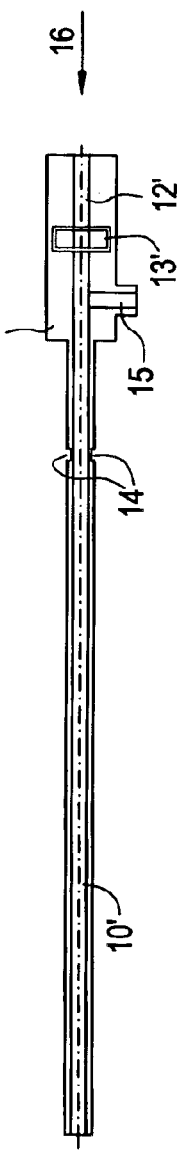
FIG. 6 shows a distally open catheter with a proximally mounted handle piece comprising a lateral infusion fitting for gas or liquid supply and an axial sealable through channel.
Figure 8:
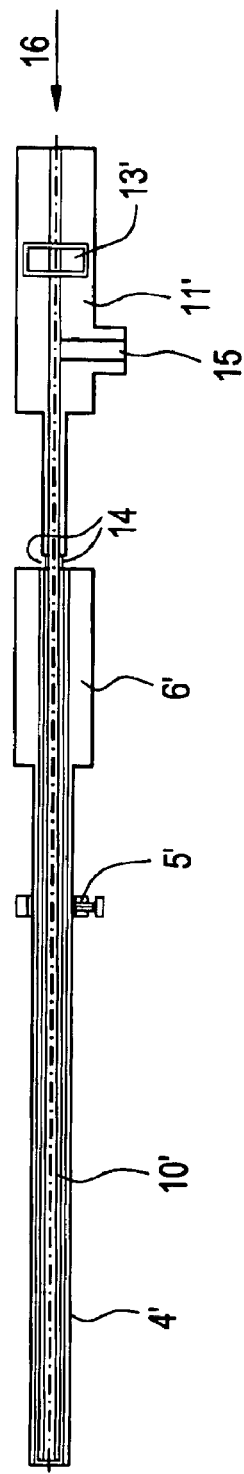
FIG. 8 shows the needle according to FIG. 5 with a catheter according to FIG. 6 inserted into it wherein the liquid or gaseous medium is conducted to the tissue directly via the energy-releasing zone of an energy guide to be positioned in the catheter and wherein the positioning of this catheter is indicated by a marking on it.

Another embodiment shown in FIG. 8 is a combination of the mandrin 1 shown in FIG. 4 and the needle 4' shown in FIG. 5 into which a catheter 10' according to FIG. 6 is inserted after the needle has been introduced into the tissue and the mandrin 1 has been removed. The needle 4' proximally comprises a handle piece 6' with a through channel 7' and an adjustable stop 5'. The catheter 10' is longer than the needle 4' but comprises a marking 14 where the two distal ends of the needle and the catheter are flush. The catheter 10' is sealed and fixed in the needle 4' using a conduit gland (not shown). In this case, the catheter 10' is proximally equipped with a handle piece 11' that is designed like the handle 6 of the needle 4 shown in FIG. 2 and comprises a through channel 12' with a seal 13' as well as an infusion fitting 15 for the direct supply of a liquid or gaseous cooling, ablation, and/or contrast agent to the diffusing body (energy-releasing zone) of a laser light guide (energy guide) inserted into the catheter 10' and to the tissue to be treated. The fitting 15 (9) is preferably a Luer lock connection while an annular packing ring with a screw-on crimped connection is provided as the seal (8, 13, 13'). Before the energy guide 16 is activated, the needle 4' is pulled back from the tissue to the stop on the handle piece 11' so that the distal end of the catheter 10' projects from the needle 4' beyond the end of the energy-releasing zone of the energy guide and does not obstruct the energy release into the tissue. The tissue access system according to the invention is to be explained in greater detail below by comparative tests in bovine liver. The performance of the principle according to the invention is compared to that of the state of the art (DE 197 02 898 A1).

The function of these systems is based on the application of high-energy laser light to heat up the tissue which results in protein coagulation. The size of the tissue zone heated up depends on the power of the laser light (wattage) and on the fact that fourth-degree burning of the tissue in the vicinity of the energy-releasing zone is undesirable as it destroys the zone by overheating. The energy-releasing zone of the light guides is cooled to prevent overheating and fourth-degree burns.

The state of the art is represented by DE 197 002 898 A1. The system comparison below is therefore based on systems with coolant supply and discharge.

Typical Use (Power Limit)

| Characteristic | DE 197 02 898 A1<br>Somatex Power applicator | Present invention<br>Mikrokath |
| --- | --- | --- |
| Watts (max.) | 25 | 15 |
| Cooling, ml/min | 60 | 0.75 |
| Discharge of cooling liquid | recirculation | into the tissue |

Comparative tests were run with both systems using fresh bovine liver; the heated zone and the basically harmless but undesirable overheating are easily identifiable after cutting the tissue open by light discoloration (protein coagulation) and blackening, respectively.

Materials

1.) Somatex Power laser application set, direct-flow cooling at 60 ml/min, outer diameter approx. 3 mm according to manufacturers specifications.
2.) Mikrokath according to DPA 101 01 143.1, infusion cooling, outer diameter 1.37 mm (tests no. 1–3) or 1.80 mm (tests no. 4–6).
3.) For both systems: A13-0540 Mikrodom applicator by Hüttinger GmbH, Umkirch, or H-6111-T3 diffusor tip laser guide connected to Dornier Fibertom by Dornier Medizin Laser GmbH.

Method

The respective applicator systems are placed deep inside the bovine liver, the light guide is inserted, laser irradiation is carried out under the conditions specified. Then the liver is cut open in parallel to the path the light guide is conducted and the light discoloration due to protein coagulation is measured. The tests denoted "P1" through "P6" (see Table 1) refer to treatment with the Somatex Power applicator set, the ones denoted "1" through "6" (see Table 1) to treatments using the Mikrokath. The coagulation volume was calculated from the long and short axes of the lightly discolored coagulation ellipsoids. The central zone frequently shows undesirable blackening (carbonization) which prevents further heat diffusion.

TABLE 1

Test overview

| No. | Light guide | Power [W] | Duration [min] | Energy [kJ] | Coolant flow [ml/min] | Additional treatment using the needle | Coagulation volume [ml] | Blackening |
|---|---|---|---|---|---|---|---|---|
| P1 | Hüttinger | 30 | 10 | 18.0 | 60 | | 25.6 | ++ |
| P2 | Hüttinger | 25 | 10 | 15.0 | 60 | | 14.4 | ++ |
| P3 | Dornier | 25 | 10 | 15.0 | 60 | | 14.1 | + |
| P4 | Dornier | 25 | 15 | 22.2 | 60 | | 41.9 | +++ |
| P5 | Dornier | 25 | 20 | 30.0 | 60 | | 28.5 | ++ |
| P6 | Dornier | 30 | 20 | 36.0 | 60 | | 63.6 | ++++ |
| 1 | Hüttinger | 12 | 20 | 14.4 | 0.50 | | 18.0 | ++ |
| 2 | Hüttinger | 12 | 20 | 14.4 | 0.50 | initially 2 ml of saline | 25.6 | + |
| 3 | Hüttinger | 12 | 20 | 14.4 | 0.50 | 2 ml of air after 0/5/10/ 15 minutes | 15.3 | none |
| 4 | Dornier | 12 | 20 | 14.4 | 0.50 | | 35.3 | + |
| 5 | Dornier | 15 | 20 | 18.0 | 0.75 | | 38.5 | + |
| 6 | Dornier | 17 | 20 | 20.4 | 0.75 | | 45.3 | +++ |

Findings and Conclusion

Despite the smaller dimensions of the Mikrokath and its considerably lower laser power, surprisingly, coagulation zones of a similar size are obtained as with the Somatex Power applicator. It is assumed that the intense coolant flow of the Somatex system discharges some of the energy from the tissue. It is as astonishing that there is no more extended central tissue blackening when using the Mikrokath although the coolant flow is reduced to 2%. The system according to the invention is as powerful as prior art but considerably simpler in design, easier to handle, leaves only minor puncture damage and is also suitable for pulmonary metastases.

| List of reference symbols | |
|---|---|
| 1, 1' | Mandrin |
| 2, 2' | Tip of 1, 1' |
| 3, 3' | Handle |
| 4, 4' | Needle |
| 5, 5' | Adjustable stop |
| 6, 6' | Handle of 4, 4' |
| 7, 7' | Through channel of 6, 6' |
| 8 | Seal of 6 |
| 9 | Infusion fitting of 6 |
| 10, 10' | Catheter |
| 11, 11' | Handle of 10, 10' |
| 12, 12' | Through channel of 11, 11' |
| 13, 13' | Seal of 11 |
| 14 | Marking |
| 15 | Infusion fitting of 11' |
| 16 | Energy guide (laser light guide) |

What is claimed is:

1. A sterile tissue access and treatment system comprising a distally open small-diameter light energy transparent elongated tube (4) formed of a non-ferromagnetic, heat-resistant material and having a proximally mounted handle piece (6), with an infusion fitting (9) for supplying an infusion medium, and with a through channel (7) that is in axial alignment with the elongated tube (4) and into which an adjustable seal (8) is integrated, and a mandrin (1) for tissue access fitted into the elongated tube (4) and distally projecting from it, said mandrin being replaceable by an energy guide (16) for tissue treatment, an annular flow channel being formed between said energy guide (16) and the elongated tube for unidirectional flow of a medium that cools the energy guide and that is discharged into the tissue after being heated by the energy guide, and the distal end of said energy guide (16) ending inside said elongated tube.

2. The tissue access and treatment system according to claim 1, characterized in that the energy guide (16) is provided in a distally closed energy transparent catheter (10) with a proximally mounted handle piece (11), in a through channel (12) of which an adjustable seal (13) is arranged for sealing off and fixing the energy guide (16), wherein said annular flow channel is between the catheter (10) and the elongated tube (4) and remains open, and the distal end of the catheter (10) does not project beyond the elongated tube (4).

3. A sterile tissue access and treatment system comprising a distally open small-diameter energy transparent elongated tube (4') formed of a non-ferromagnetic, heat-resistant material, and having a proximally mounted handle piece (6') with a through channel (7') that is in axial alignment with the elongated tube (4'), and wherein a mandrin (1') for tissue access is fitted gastight into the elongated tube (4') and the through channel (7') and projects distally from the elongated tube (4'), and wherein, for tissue treatment, a distally open catheter (10') having a proximally mounted handle piece (11') with a through channel (12') provided with an adjustable seal (13') and an infusion fitting (15) is introduced into the elongated tube, with an energy guide (16) arranged inside the catheter (10'), forming an annular flow channel for unidirectional flow of an infusion medium that cools the energy guide and that is discharged into the tissue after being heated by the energy guide, and being sealed and fixed into said handle piece (11') using the seal (13').

4. The tissue access and treatment system according to claim 3, characterized in that the catheter (10') is longer than the elongated tube (4') and has a marking (14) for positioning its distal end relative to the distal end of the elongated tube.

5. The tissue access and treatment system according to claim 2 or 4, characterized in that the catheter (10, 10') is formed, at least in a section that houses an energy-releasing zone of the energy guide (16), of a heat-resistant and energy-transparent material and in that the elongated tube (4, 4'), at least in this section, is formed of an energy-transparent material.

6. The tissue access and treatment system according to claim 1, 2 or 3, characterized in that the seal (8, 13, 13') in the through channel (7, 12, 12') of the handle piece (6, 11, 11') is an adjustable packing ring with a screw-on crimped connection.

7. The tissue access and treatment system according to claim 1, 2 or 3, characterized in that a conduit gland is provided as the seal (8, 13, 13').

8. The tissue access and treatment system according to claim 2 or 3, characterized in that the energy-transparent elongated tube and catheter are permeable to sound and infrared light of longer wave length.

9. The tissue access and treatment system according to claim 1 or 3, characterized in that the energy guide (16) comprises a diffusing body at an energy-releasing distal end.

10. The tissue access and treatment system according to claim 1 or 3, characterized in that a stop (5, 5') that can be adjusted in a longitudinal direction is mounted to the elongated tube to limit puncture depth.

11. The tissue access and treatment system according to claim 1 or 3, characterized in that a sterile pharmaceutical sealing liquid is present in narrowest gaps between the elongated (4, 4') and the mandrin (1) to prevent air from entering the organ to be treated.

12. The tissue access and treatment system according to claim 1 or 3, characterized in that the energy guide (16) is connected to a laser light source or an infrared radiation source or a short-wave sound source or a vapor source.

13. The tissue access and treatment system according to claim 1 or 3, characterized in that the infusion fitting (9, 15) is connected to one of a gaseous or liquid media reservoir for providing at least one of a sealing agent, a coolant and heat transport medium, a contrast agent, an ablation agent, and a therapeutic agent.

14. The tissue access and treatment system according to claim 1 or 3, characterized in that a cooling medium is conducted past the energy guide at a very slow flow rate of 0.1 to 5 ml/min during the thermal tissue treatment through energy release.

* * * * *

UNITED STATES PATENT AND TRADEMARK OFFICE
CERTIFICATE OF CORRECTION

PATENT NO. : 6,899,708 B2
DATED : May 31, 2005
INVENTOR(S) : Ulrich Speck et al.

It is certified that error appears in the above-identified patent and that said Letters Patent is hereby corrected as shown below:

Column 9,
Line 18, after "elongated" insert -- tube --.

Signed and Sealed this

Twenty-seventh Day of September, 2005

JON W. DUDAS
*Director of the United States Patent and Trademark Office*